(12) United States Patent
Zhu et al.

(10) Patent No.: US 11,180,443 B2
(45) Date of Patent: *Nov. 23, 2021

(54) PREPARATION METHOD FOR M-DIAMIDE COMPOUNDS

(71) Applicant: CAC Nantong Chemical Co., LTD, Jiangsu Province (CN)

(72) Inventors: Jintao Zhu, Jiangsu Province (CN); Liang Lv, Jiangsu Province (CN); Chaoqun Huang, Jiangsu Province (CN); Liangming Luo, Jiangsu Province (CN); Rong Zhang, Jiangsu Province (CN)

(73) Assignee: CAC Nantong Chemical Co., LTD, Nantong (CN)

( * ) Notice: Subject to any disclaimer, the term of this patent is extended or adjusted under 35 U.S.C. 154(b) by 113 days.

This patent is subject to a terminal disclaimer.

(21) Appl. No.: 16/847,370

(22) Filed: Apr. 13, 2020

(65) Prior Publication Data
US 2021/0122707 A1 Apr. 29, 2021

(30) Foreign Application Priority Data
Oct. 25, 2019 (CN) .......................... 201911023386.7

(51) Int. Cl.
*C07C 231/14* (2006.01)
(52) U.S. Cl.
CPC .................................. *C07C 231/14* (2013.01)
(58) Field of Classification Search
CPC .................................................... C07C 231/14
See application file for complete search history.

(56) References Cited

U.S. PATENT DOCUMENTS

| 9,890,110 B2 | 2/2018 | Aoki et al. |
| 2015/0065721 A1 | 3/2015 | Okura |

FOREIGN PATENT DOCUMENTS

| CN | 109497062 | 3/2019 |
| EP | 2319830 A1 | 5/2011 |
| EP | 2835366 A1 | 2/2015 |
| JP | 35262201 | 5/1977 |
| JP | 36075443 | 4/1985 |
| JP | H0827054 | 1/1996 |
| JP | 2000516941 | 12/2000 |
| JP | 2009013158 | 1/2009 |
| JP | 2010047478 | 3/2010 |
| JP | 2011529939 | 12/2011 |
| WO | 2010015559 | 2/2010 |
| WO | 2013/150988 | 10/2013 |
| WO | WO-2019059412 A1 * | 3/2019 ............. A01N 43/54 |

OTHER PUBLICATIONS

Luo et al. Development of an Efficient Synthetic Process for Broflanilide, Org. Process Res. Dev. 2020, vol. 24, No. 6, Jun. 19, 2020, pp. 1042-1031. XP055730033.
European Search Report, Application No. 20164171.9, dated Oct. 7, 2020.
Office Action issued by the Japanese Patent Office for Application No. 2020-005077, date of drafting Dec. 16, 2020, English translation attached.
Office Action issued by the India Patent Office for Application No. 202024015968, date of dispatch May 25, 2021.

* cited by examiner

*Primary Examiner* — Yong L Chu
(74) *Attorney, Agent, or Firm* — Barnes & Thornburg LLP; Jeffrey R. Stone

(57) ABSTRACT

The present disclosure provides a preparation method for m-diamide compounds. The method includes the following steps: 2-fluoro-3-nitrobenzoyl chloride and 4-(perfluoropropane-2-yl)-2-(trifluoromethyl)aniline are subjected to a condensation reaction, followed by a reduction reaction and an alkylation reaction to give 2-fluoro-3-(alkylamino)-N-(4-(perfluoropropane-2-yl)-2-(trifluoromethyl)phenyl)benzamide, which reacts with an acyl chloride compound to give 2-fluoro-3-(alkylbenzamido)-N-(4-(perfluoropropane-2-yl)-2-(trifluoromethyl)phenyl)benzamide, which is finally brominated to obtain the m-diamide compound. The reactions are almost quantitative with few by-products. Cryogenic and high-temperature reactions are not used. The introduction of bromine atoms at specific sites can be achieved in the final step. The preparation method has high yield and is more suitable for industrial production.

20 Claims, No Drawings

PREPARATION METHOD FOR M-DIAMIDE COMPOUNDS

CROSS-REFERENCE TO RELATED APPLICATIONS

The application claims the benefit of the earlier filing date of Chinese Patent Application No. 201911023386.7, filed on Oct. 25, 2019 to the China National Intellectual Property Administration, the contents of which are incorporated by reference herein in its entirety.

TECHNICAL FIELD

The present disclosure belongs to the technical field of pesticide and insecticide synthesis, relates to a preparation method for m-diamide compounds, and particularly to a preparation method for an amide insecticide Broflanilide and its analogue Cyprofluoranilide.

BACKGROUND

Broflanilide is a m-bisamide compound, specifically in a structure of m-formylaminobenzamide. Its chemical structure and mechanism of action are significantly different from the existing o-bisamide insecticides such as chlorantraniliprole. Broflanilide not only has efficient insecticidal activity against pests chewing crops such as Lepidoptera and Coleoptera on crops such as fruits, vegetables, beans and rice, but also can effectively control pests that are resistant to other insecticides, especially pests that are resistant to chlorantraniliprole and fipronil. The m-diamide compounds represented by Broflanilide are increasingly becoming research hotspots of pesticide companies at home and abroad due to their characteristics such as unique action mechanisms, novel action targets and environmental friendliness. Analogues of Broflanilide have become one of the most promising research and development directions of pesticides.

Cyprofluoranilide (Compound No. 62) disclosed in CN109497062A is a new insecticide developed on the basis of Broflanilide. It has high insecticidal activity at low dosage and take effect rapidly, which can exert insecticidal activity after one day of application and achieve very high insecticidal activity within 3 days, thus has a good quick-acting effect.

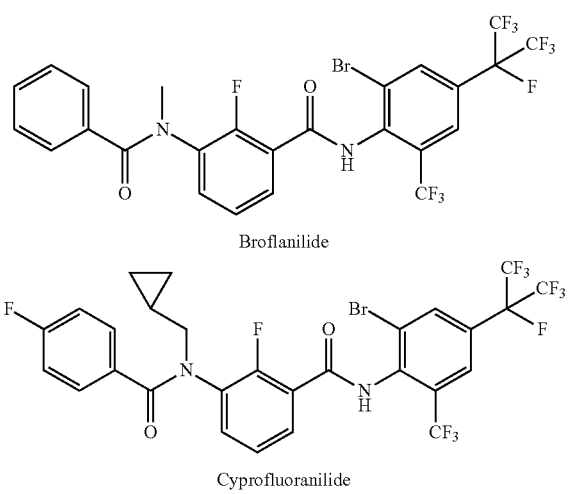

There are mainly three routes currently reported for synthesis of Broflanilide. A reported synthetic route for Cyprofluoranilide is similar to that of Broflanilide, except that substituents are different.

Route I

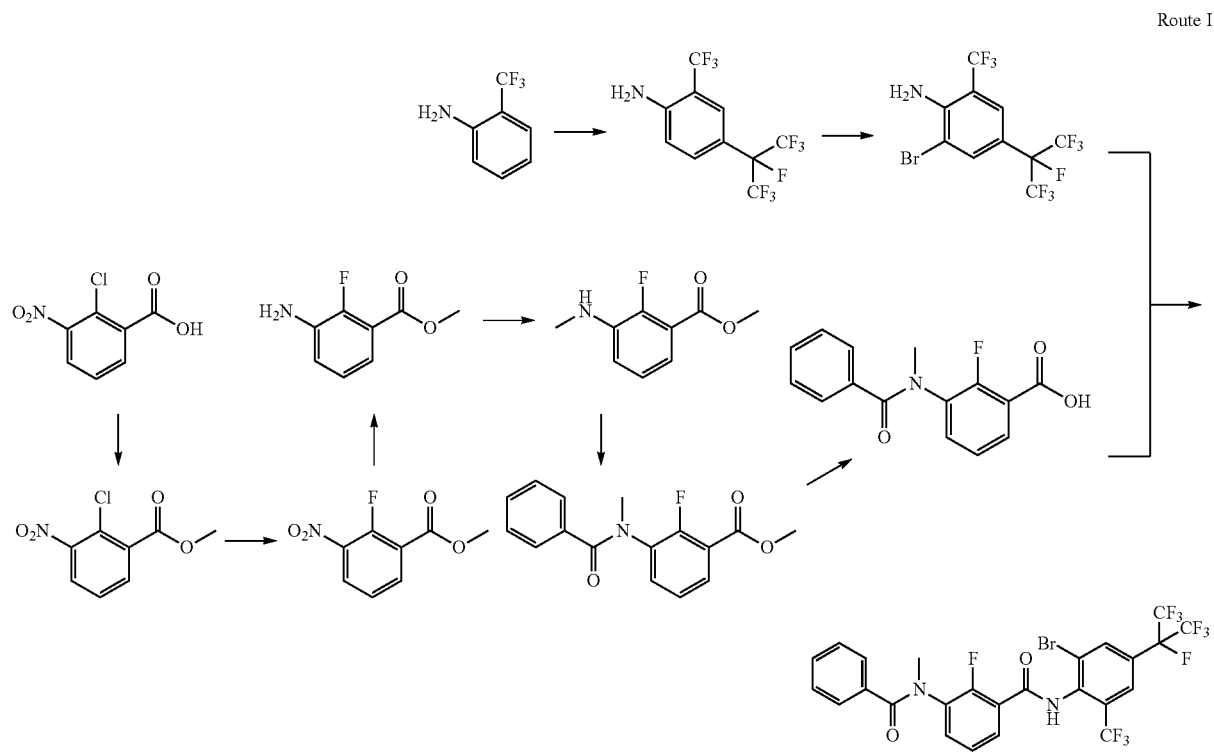

Specifically, Route I has the following disadvantages: it has a long process route; when Broflanilide is prepared at the last step, diamide byproduct is generated; the amount of acid used is at least 2.4 times more than that of amine; moreover, alkali has to be added for hydrolyzation; at the same time, an acid recovery operation is required; after the hydrolyzation, both of the aqueous phase and the oil phase are too dark to be differentiated and separated during the phase separation. The last step yield of Broflanilide preparation is about 75%.

Furthermore, in Route 1, it was found that, during preparation of acyl chloride, the amide structure of the acid broke to generate benzoyl chloride, which resulted in impurities difficult to be removed during condensation reaction with the amine for preparing Broflanilide.

Route II

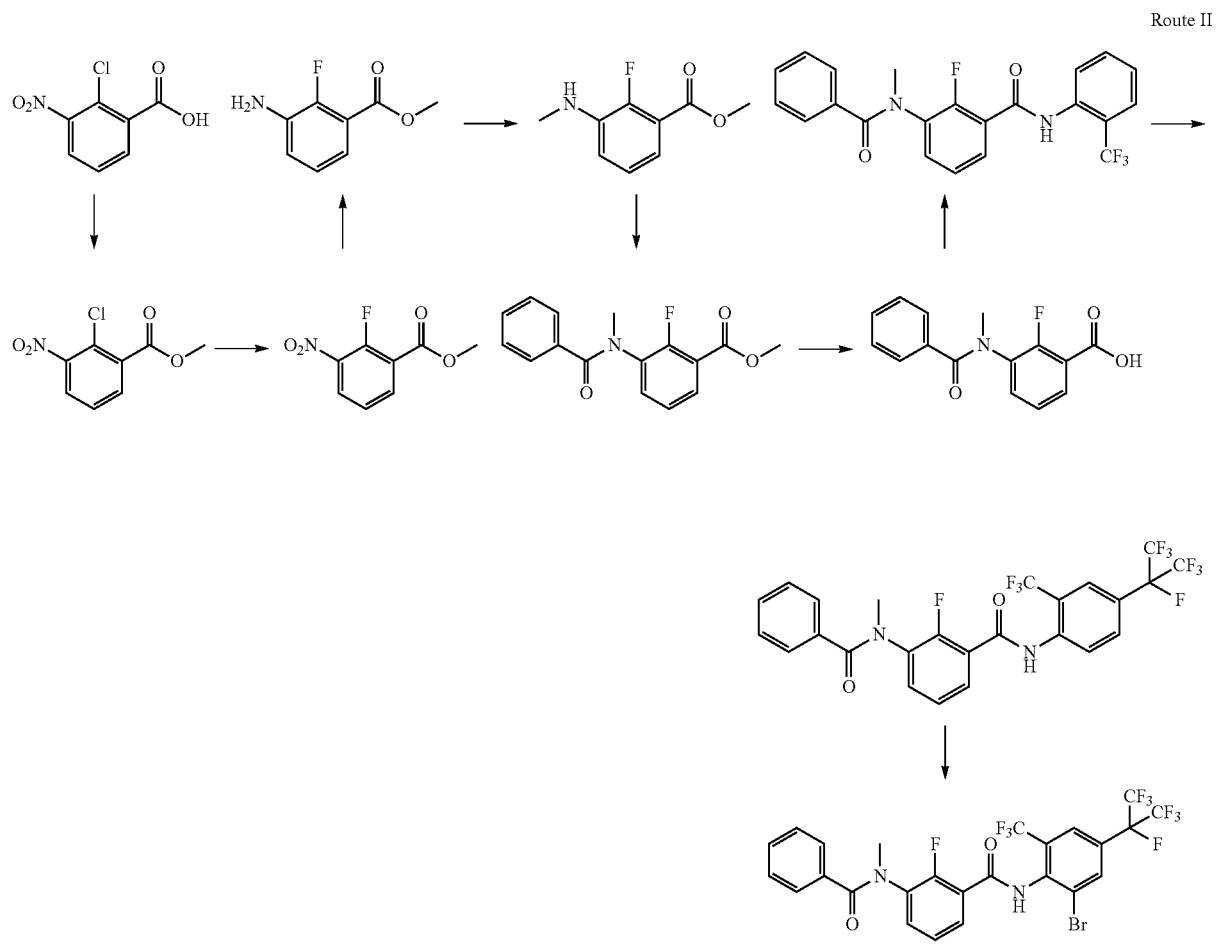

Route II also has the disadvantage of a long process route. The yield of the eighth step for installing heptafluoroisopropyl is only 63%, thus it is difficult to purify the desired intermediate. Moreover, in the final bromination step for preparing Broflanilide, expensive NBS reagent is used.

Route III

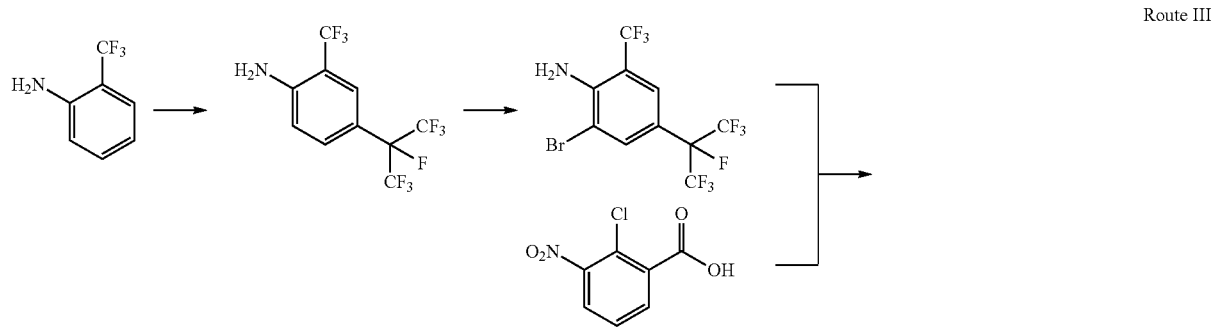

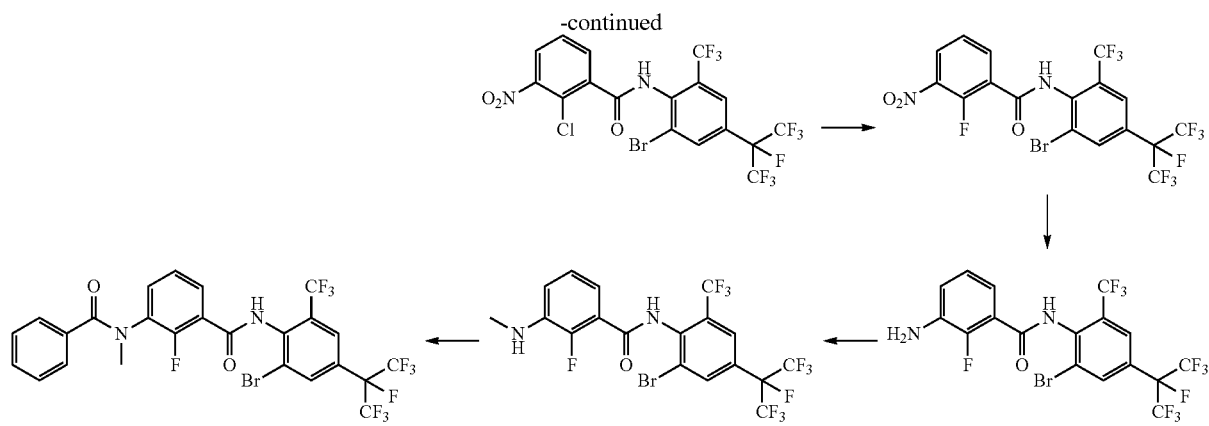

In Route III, in condensation of 2-chloro-3-nitrobenzoic acid with the amine, lithium diisopropylamide is used, which is costly and requires deep cooling at −70° C., thus it is difficult to be industrialized; the single step yield is only 34%, which is not conducive to industrial production.

As mentioned above, since existing synthetic methods for preparing Broflanilide and Cyprofluoranilide have disadvantages such as not environment-friendly, low yield, and hard to purify, there is a need to develop more suitable synthetic processes.

SUMMARY

The present disclosure provides a preparation method for m-diamide compounds, in particular a preparation method for an insecticide Broflanilide and its analogue Cyprofluoranilide. In such method, the synthetic route is short, a few steps are almost quantitative with few by-products, and deep cooling and high-temperature reactions are not used, thus it is more suitable for industrial production. Moreover, the method needs no separation after each preparation step, or the purification can be carried out by using different solvents to obtain high-quality final products.

The present disclosure adopts the following technical solutions:

In one aspect, the present disclosure provides a preparation method for m-diamide compounds having a structure of formula I, wherein the preparation method comprises the following steps:

(1) 2-fluoro-3-nitrobenzoyl chloride and 4-(perfluoropropane-2-yl)-2-(trifluoromethyl)aniline (referred to as decafluoroaniline in the present disclosure) are subjected to a condensation reaction to give 2-fluoro-3-nitro-N-(4-(perfluoropropane-2-yl)-2-(trifluoromethyl) phenyl)benzamide (referred to as nitroamide in the present disclosure), the reaction scheme is as follows:

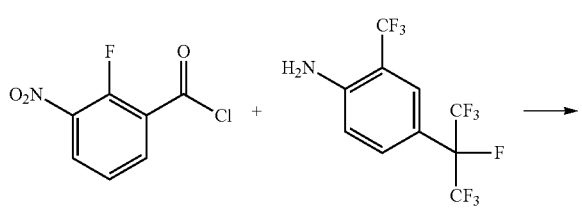

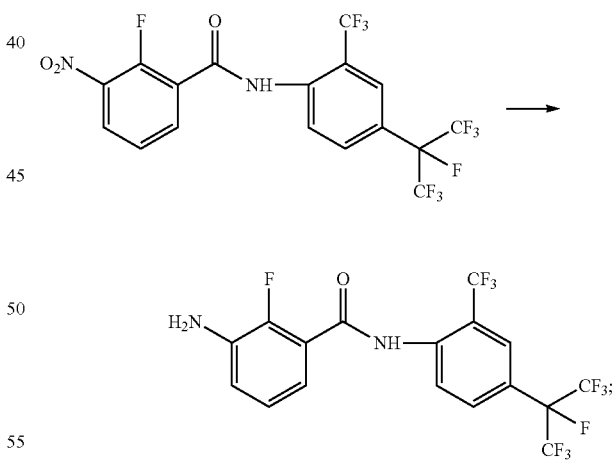

(2) 2-fluoro-3-nitro-N-(4-(perfluoropropane-2-yl)-2-(trifluoromethyl) phenyl)benzamide is subjected to a reduction reaction to give 3-amino-2-fluoro-N-(4-(perfluoropropane-2-yl)-2-(trifluoromethyl) phenyl)benzamide (referred to as aminoamide in the present disclosure), the reaction scheme is as follows:

(3) 3-amino-2-fluoro-N-(4-(perfluoropropane-2-yl)-2-(trifluoromethyl) phenyl)benzamide and an alkylating agent are subjected to an alkylation reaction to give 2-fluoro-3-(alkylamino)-N-(4-(perfluoropropane-2-yl)-2-(trifluoromethyl)phenyl)benzamide (when the alkyl group $R_1$ is methyl, it is abbreviated as methylaminoamide, and when $R_1$ is cyclopropylmethyl, it is abbreviated as cyclopropylaminoamide), the reaction scheme is as follows:

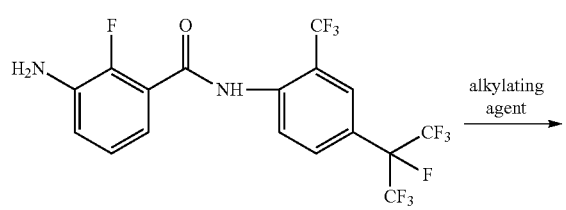 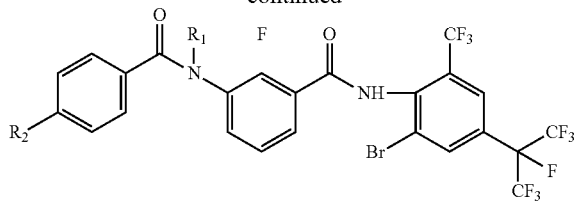

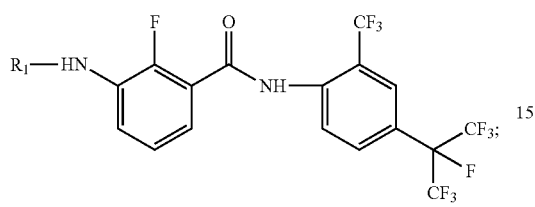

wherein, $R_1$ is methyl or (4) 2-fluoro-3-(alkylamino)-N-(4-(perfluoropropane-2-yl)-2-(trifluoromethyl)phenyl)benzamide is reacted with the acyl chloride compound as shown by formula II to give 2-fluoro-3-(alkylbenzamide)-N-(4-(perfluoropropane-2-yl)-2-(trifluoromethyl)phenyl)benzamide (when the alkyl $R_1$ is methyl, it is abbreviated as Broflanilide diamide, and when $R_1$ is cyclopropylmethyl, it is abbreviated as Cyprofluoranilide diamide), the reaction scheme is as follows:

$R_2$ is hydrogen or fluorine.

In the preparation method of the present disclosure, a few steps are almost quantitative with few by-products, and deep cooling and high-temperature reactions are not used; the introduction of bromine atoms at specific sites can be achieved in the final step; and the yield is high, thus it is more suitable for industrial production. Moreover, the method needs no separation after each preparation step, or the purification can be carried out by using different solvents to obtain high-quality final products.

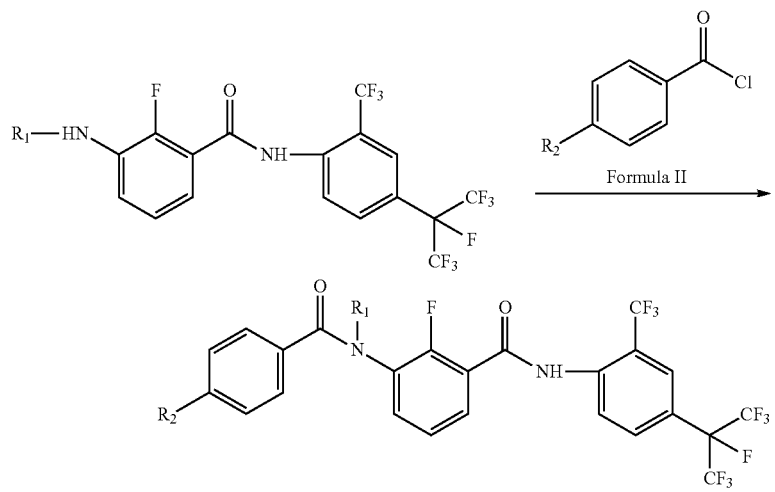

(5) 2-fluoro-3-(alkylbenzamido)-N-(4-(perfluoropropane-2-yl)-2-(trifluoromethyl)phenyl)benzamide is brominated to give the m-diamide compound represented by formula I (i.e., Broflanilide or Cyprofluoranilide), and the reaction scheme is as follows:

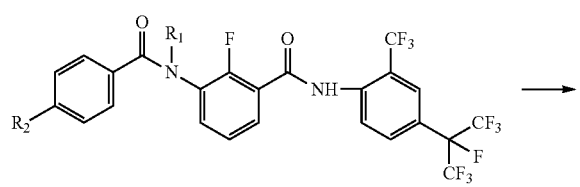

In the present disclosure, 2-fluoro-3-nitrobenzoyl chloride in step (1) can be prepared by the following method: A) 2-fluoro-3-nitrobenzoic acid is reacted with an acyl chlorinating reagent to give 2-fluoro-3-nitrobenzoyl chloride.

Preferably, the acyl chlorinating reagent in step A is one or a combination of at least two selected from the group consisting of thionyl chloride, triphosgene, oxalyl chloride, phosphorus trichloride, and phosphorus pentachloride, preferably thionyl chloride or triphosgene.

Preferably, the molar ratio of 2-fluoro-3-nitrobenzoic acid to the acyl chlorinating reagent in step A is 1:0.33 to 1:2.5, e.g., 1:0.33, 1:0.5, 1:0.7, 1:0.9, 1:1, 1:1.3, 1:1.5, 1:1.8, 1:2, 1:2.2, or 1:2.5, preferably 1:0.5 to 1:2.0.

Preferably, the solvent of the reaction in step A is anyone or a combination of at least two selected from the group consisting of dichloromethane, 1,2-dichloroethane, chloroform, benzene, toluene, xylene, chlorobenzene, and dichlorobenzene, preferably toluene and/or xylene.

Preferably, the mass ratio of 2-fluoro-3-nitrobenzoic acid to the solvent in step A is 1:1 to 1:5, e.g., 1:1, 1:1.3, 1:1.5, 1:1.8, 1:2, 1:2.3, 1:2.5, 1:2.8, 1:3, 1:3.3, 1:3.5, 1:3.8, 1:4, 1:4.3, 1:4.5, 1:4.8, or 1:5, preferably 1:2 to 1:4.

Preferably, the temperature of the reaction in step A is 40-180° C., e.g., 40° C., 50° C., 60° C., 80° C., 100° C., 120° C., 140° C., 150° C., 170° C., or 180° C., preferably 110-140° C.

Preferably, the reaction time in step A is 3-8 h, e.g., 3 h, 3.3 h, 3.5 h, 3.8 h, 4 h, 4.5 h, 4.8 h, 5 h, 5.3 h, 5.5 h, 5.8 h, 6 h, 6.5 h, 6.8 h, 7 h, 7.5 h, 7.8 h, or 8 h, preferably 4-6 h.

Preferably, in step (1), the molar ratio of 2-fluoro-3-nitrobenzoyl chloride to 4-(perfluoropropane-2-yl)-2-(trifluoromethyl)aniline is 1:1 to 1.5:1, e.g., 1:1, 1.1:1, 1.2:1, 1.3:1, 1.4:1, or 1.5:1, preferably 1.1:1 to 1.3:1.

Preferably, the solvent of the reaction in step (1) is any one or a combination of at least two selected from the group consisting of dichloromethane, 1,2-dichloroethane, chloroform, benzene, toluene, xylene, chlorobenzene, or dichlorobenzene, preferably toluene and/or xylene.

Preferably, the mass ratio of 4-(perfluoropropane-2-yl)-2-(trifluoromethyl) aniline to the solvent in step (1) is 1:1 to 1:5, e.g., 1:1, 1:1.2, 1:1.5, 1:1.8, 1:2, 1:2.2, 1:2.4, 1:2.5, 1:2.7, 1:2.8, 1:2.9, 1:3, 1:3.2, 1:3.4, 1:3.6, 1:3.8, 1:4, 1:4.3, 1:4.5, 1:4.8, or 1:5, preferably 1:2 to 1:4.

Preferably, the reaction in step (1) is performed in the presence of a catalyst, and the catalyst is 4-dimethylaminopyridine (DMAP).

Preferably, the used amount of the catalyst is 0.1%-5% by mass of 4-(perfluoropropane-2-yl)-2-(trifluoromethyl)aniline, e.g., 0.1%, 0.3%, 0.5%, 0.8%, 1%, 1.5%, 1.8%, 2%, 2.3%, 2.5%, 2.8%, 3%, 3.5%, 3.8%, 4%, 4.5%, or 5%.

Preferably, after the reaction in step (1) is completed, post-treatment is performed, and the post-treatment includes the following steps:

An alkali solution is added to the reaction mixture, stirred at 80° C. for 10-40 min (e.g., 10 min, 15 min, 18 min, 20 min, 23 min, 25 min, 28 min, 30 min, 35 min, or 40 min), followed by phase separation while it is hot, then the resulting organic layer is cooled to room temperature, then stirred at 0-5° C. (e.g., 0° C., 1° C., 2° C., 3° C., 4° C., or 5° C.) for 1-3 h (e.g., 1 h, 1.3 h, 1.5 h, 1.8 h, 2 h, 2.3 h, 2.5 h, 2.8 h, or 3 h), filtered and dried to give 2-fluoro-3-nitro-N-(4-(perfluoropropane-2-yl)-2-(trifluoromethyl) phenyl)benzamide.

In the post-treatment after the completion of the reaction described in step (1), after addition of the alkali solution, the temperature of stirring should be maintained at 80° C. If the temperature is too low, the material will precipitate out, and if the temperature is too high, side reactions will occur.

Preferably, the alkali solution is one or a combination of at least two selected from the group consisting of aqueous solutions of hydroxide, carbonate or bicarbonate of an alkali metal or an alkaline earth metal, and is preferably a sodium hydroxide solution or a sodium carbonate solution.

Preferably, the temperature of the condensation reaction in step (1) is 40-180° C., e.g., 40° C., 50° C., 60° C., 80° C., 100° C., 120° C., 140° C., 150° C., 170° C., or 180° C., preferably 110-140° C.

Preferably, the time of the condensation reaction in step (1) is 3-8 h, e.g., 3 h, 3.3 h, 3.5 h, 3.8 h, 4 h, 4.5 h, 4.8 h, 5 h, 5.3 h, 5.5 h, 5.8 h, 6 h, 6.5 h, 6.8 h, 7 h, 7.5 h, 7.8 h, or 8 h, preferably 4-6 h.

Preferably, the catalyst for the reduction reaction in step (2) is any one of palladium-carbon, platinum-carbon, and Raney nickel, preferably palladium-carbon or platinum-carbon catalyst.

Preferably, the content of an active substance in the catalyst is not less than 10%, preferably 10% palladium-carbon catalyst.

Preferably, in step (2), the mass ratio of 2-fluoro-3-nitro-N-(4-(perfluoropropane-2-yl)-2-(trifluoromethyl) phenyl) benzamide to the catalyst is 1:0.001 to 1:0.01, e.g., 1:0.001, 1:0.003, 1:0.004, 1:0.005, 1:0.006, 1:0.007, 1:0.008, or 1:0.01, preferably 1:0.003 to 1:0.006.

Preferably, the reductant of the reduction reaction in step (2) is hydrogen.

Preferably, in the reduction reaction in step (2), the pressure after introducing hydrogen is controlled to be 1.5-3.0 MPa, e.g., 1.5 MPa, 1.7 MPa, 1.9 MPa, 2 MPa, 2.2 MPa, 2.5 MPa, 2.8 MPa, or 3 MPa, preferably 2.0-2.5 MPa.

Preferably, the temperature of the reduction reaction in step (2) is 25-120° C., e.g., 25° C., 30° C., 40° C., 50° C., 60° C., 70° C., 80° C., 90° C., 100° C., 110° C., or 120° C., preferably 40-100° C.

Preferably, the time of the reduction reaction in step (2) is 8-16 h, e.g., 8 h, 9 h, 10 h, 11 h, 12 h, 13 h, 14 h, 15 h, or 16 h, preferably 10-14 h.

Preferably, the alkylating agent in step (3) is formaldehyde or cyclopropanecarboxaldehyde.

Preferably, when the alkylating agent in step (3) is formaldehyde, the molar ratio of 3-amino-2-fluoro-N-(4-(perfluoropropane-2-yl)-2-(trifluoromethyl)phenyl)benzamide to formaldehyde is 1:2 to 1:8, e.g., 1:2, 1:2.5, 1:2.8, 1:3, 1:3.3, 1:3.5, 1:3.8, 1:4, 1:4.5, 1:5, 1:5.5, 1:5.8, 1:6, 1:6.5, 1:6.8, 1:7, 1:7.5, 1:7.8, or 1:8, preferably 1:4 to 1:6.

Preferably, when the alkylating reagent in step (3) is formaldehyde, the alkylation reaction is performed in the presence of concentrated sulfuric acid; the concentrated sulfuric acid is also used as a solvent in step (3).

Preferably, the mass ratio of 3-amino-2-fluoro-N-(4-(perfluoropropane-2-yl)-2-(trifluoromethyl)phenyl)benzamide to the concentrated sulfuric acid is 1:3 to 1:10, e.g., 1:3, 1:3.3, 1:3.5, 1:3.8, 1:4, 1:4.3, 1:4.5, 1:4.8, 1:5, 1:5.5, 1:6, 1:6.5, 1:7, 1:7.5, 1:8, 1:8.5, 1:9, 1:9.5, or 1:10, preferably 1:4 to 1:6.

Preferably, when the alkylating reagent in step (3) is formaldehyde, the temperature of the alkylation reaction in step (3) is 25-100° C., e.g., 25° C., 50° C., 55° C., 60° C., 65° C., 70° C., 75° C., 80° C., 85° C., 90° C., 95° C., or 100° C., preferably 50-80° C.

Preferably, when the alkylating reagent in step (3) is formaldehyde, the time of the alkylation reaction in step (3) is 12-24 h, e.g., 12 h, 14 h, 16 h, 18 h, 20 h, 22 h, or 24 h, preferably 14-18 h.

Preferably, when the alkylating reagent in step (3) is cyclopropanecarboxaldehyde, the alkylation reaction in step (3) is performed in the presence of zinc powder.

Preferably, the molar ratio of 3-amino-2-fluoro-N-(4-(perfluoropropane-2-yl)-2-(trifluoromethyl)phenyl)benzamide to zinc powder is 1:1.5 to 1:6, e.g., 1:1.5, 1:1.8, 1:2, 1:2.5, 1:2.8, 1:3, 1:3.5, 1:3.8, 1:4, 1:4.5, 1:4.8, 1:5, 1:5.5, 1:5.8, or 1:6, preferably 1:2 to 1:4.

Preferably, when the alkylating agent in step (3) is cyclopropanecarboxaldehyde, the molar ratio of 3-amino-2-fluoro-N-(4-(perfluoropropane-2-yl)-2-(trifluoromethyl) phenyl)benzamide to cyclopropanecarboxaldehyde is 1:1.2 to 1:3, e.g., 1:1.2, 1:1.5, 1:1.8, 1:2, 1:2.3, 1:2.5, 1:2.8, or 1:3, preferably 1:1.6 to 1:2.

Preferably, when the alkylating reagent in step (3) is cyclopropanecarboxaldehyde, the alkylation reaction in step (3) is performed in the presence of acetic acid.

Preferably, the molar ratio of 3-amino-2-fluoro-N-(4-(perfluoropropane-2-yl)-2-(trifluoromethyl)phenyl)benzamide to acetic acid is 1:3 to 1:12, e.g., 1:3, 1:3.5, 1:3.8, 1:4, 1:4.5, 1:5, 1:5.5, 1:6, 1:6.5, 1:7, 1:7.5, 1:8, 1:9, 1:10, 1:11, or 1:12, preferably 1:4 to 1:8.

Preferably, when the alkylating reagent in step (3) is cyclopropanecarboxaldehyde, the temperature of the alkylation reaction is 30-90° C., e.g., 30° C., 40° C., 50° C., 60° C., 70° C., 80° C., or 90° C., preferably 40-80° C.

Preferably, when the alkylating reagent in step (3) is cyclopropanecarboxaldehyde, the time of the alkylation reaction is 1-4 h, e.g., 1 h, 1.5 h, 1.8 h, 2 h, 2.5 h, 2.8 h, 3 h, 3.3 h, 3.5 h, 3.8 h, or 4 h, preferably 1.5-2.5 h.

Preferably, when the alkylating reagent in step (3) is cyclopropanecarboxaldehyde, the solvent of the alkylation reaction is one or a combination of at least two selected from the group consisting of methanol, ethyl acetate, 1,2-dichloroethane, toluene, and xylene, preferably is one or a combination of at least two selected from the group consisting of ethyl acetate, toluene, and xylene.

Preferably, in step (4), the molar ratio of the 2-fluoro-3-(alkylamino)-N-(4-(perfluoropropane-2-yl)-2-(trifluoromethyl) phenyl) benzamide to the acyl chloride compound represented by formula II is 1:1 to 1:1.5, e.g., 1:1, 1:1.1, 1:1.2, 1:1.3, 1:1.4, or 1:1.5, preferably 1:1.05 to 1:1.1.

Preferably, the reaction in step (4) is performed in the presence of a catalyst, and the catalyst is 4-dimethylaminopyridine (DMAP).

Preferably, the used amount of the catalyst is 0.1%-5% by mass of 2-fluoro-3-(alkylamino)-N-(4-(perfluoropropane-2-yl)-2-(trifluoromethyl)phenyl)benzamide, e.g., 0.1%, 0.3%, 0.5%, 0.8%, 1%, 1.5%, 1.8%, 2%, 2.3%, 2.5%, 2.8%, 3%, 3.5%, 3.8%, 4%, 4.5%, or 5%.

Preferably, the solvent of the reaction in step (4) is any one or a combination of at least two of the group consisting of dichloromethane, 1,2-dichloroethane, chloroform, benzene, toluene, xylene, chlorobenzene, and dichlorobenzene, preferably 1,2-dichloroethane or toluene.

Preferably, in step (4), the mass ratio of 2-fluoro-3-(alkylamino)-N-(4-(perfluoropropane-2-yl)-2-(trifluoromethyl)benzamide to the solvent is 1:2 to 1:8, e.g., 1:2, 1:2.5, 1:2.8, 1:3, 1:3.5, 1:3.8, 1:4, 1:4.5, 1:5, 1:5.5, 1:6, 1:6.5, 1:7, 1:7.5, or 1:8, preferably 1:4 to 1:6.

Preferably, the temperature of the reaction in step (4) is 40-180° C., e.g., 40° C., 50° C., 60° C., 80° C., 100° C., 120° C., 140° C., 150° C., 170° C., or 180° C., preferably 80-110° C.

Preferably, the time of the reaction in step (4) is 1-6 h, e.g., 1 h, 1.5 h, 2 h, 2.5 h, 3 h, 3.5 h, 4 h, 4.5 h, 5 h, 5.5 h, or 6 h, preferably 3-5 h.

Preferably, after the reaction in step (4) is completed, post-treatment is performed, and the post-treatment includes the following steps:

An alkali solution is added to the reaction mixture, stirred at 80° C. for 10-40 min (e.g., 10 min, 15 min, 18 min, 20 min, 25 min, 30 min, 35 min, or 40 min), followed by phase separation while it is hot, to obtain 2-fluoro-3-(alkylbenzamido)-N-(4-(perfluoropropane-2-yl)-2-(trifluoromethyl)phenyl)benzamide.

In post-treatment after the completion of the reaction described in step (4), after the addition of the alkali solution, the temperature of stirring should be maintained at 80° C. If the temperature is too low, the material will precipitate out, and if the temperature is too high, side reactions will occur.

Preferably, the alkali solution is one or a combination of at least two selected from the group consisting of aqueous solutions of hydroxide, carbonate or bicarbonate of an alkali metal or an alkaline earth metal, preferably a sodium hydroxide solution or a sodium carbonate solution.

Preferably, the bromination reaction in step (5) is performed in the presence of bromide and oxidant.

Preferably, the bromide is one or a combination of at least two selected from the group consisting of an alkali metal bromide, an alkaline earth metal bromide, hydrobromic acid, bromine, and ammonium bromide, preferably sodium bromide or hydrobromic acid.

Preferably, in step (5), the molar ratio of 2-fluoro-3-(alkylbenzamido)-N-(4-(perfluoropropane-2-yl)-2-(trifluoromethyl)phenyl)benzamide to bromide is 1:0.55 to 1:2.0, e.g., 1:0.55, 1:0.7, 1:0.9, 1:1, 1:1.2, 1:1.4, 1:1.6, 1:1.8, or 1:2, preferably 1:1.2 to 1:1.6.

Preferably, the oxidant is one or a combination of at least two selected from the group consisting of chlorine gas, perchlorate, chlorate, chlorite, and hypochlorite of alkali metal or alkaline earth metal, preferably one or a combination of at least two selected from the group consisting of sodium chlorate, sodium hypochlorite, and chlorine gas.

Preferably, in step (5), the molar ratio of 2-fluoro-3-(alkylbenzamido)-N-(4-(perfluoropropane-2-yl)-2-(trifluoromethyl)phenyl)benzamide to oxidant is 1:0.2 to 1:2.0, e.g., 1:0.2, 1:0.4, 1:0.55, 1:0.7, 1:0.9, 1:1, 1:1.2, 1:1.4, 1:1.6, 1:1.8, or 1:2, preferably 1:0.4 to 1:1.6.

Preferably, the bromination reaction in step (5) is performed in the presence of an alkaline substance.

Preferably, the alkaline substance is one or a combination of at least two selected from the group consisting of hydroxide, carbonate and bicarbonate of an alkali metal or an alkaline earth metal, preferably sodium hydroxide or potassium hydroxide.

Preferably, the molar ratio of 2-fluoro-3-(alkylbenzamido)-N-(4-(perfluoropropane-2-yl)-2-(trifluoromethyl) phenyl)benzamide to the alkaline substance is 1:0 to 1:3.0, e.g., 1:0.3, 1:0.5, 1:0.8, 1:1, 1:1.5, 1:1.8, 1:2, 1:2.2, 1:2.5, 1:2.8, or 1:3, preferably 1:0.5 to 1:2.8.

Preferably, the temperature of the bromination reaction in step (5) is 0-150° C., e.g., 0° C., 5° C., 10° C., 20° C., 25° C., 30° C., 40° C., 50° C., 60° C., 70° C., 80° C., 90° C., 100° C., 110° C., 120° C., 130° C., 140° C., or 150° C., preferably 40-90° C.

Preferably, the time of the bromination reaction in step (5) is 0.5-8 h, e.g., 0.5 h, 0.6 h, 0.8 h, 1 h, 1.5 h, 1.8 h, 2 h, 2.5 h, 3 h, 4 h, 5 h, 6 h, 7 h, or 8 h, preferably 1-2 h.

In the present disclosure, after the reaction in step (5) is completed, the reaction solution is subjected to phase separation while it is hot, an organic layer is separated and washed by adding sodium sulfite solution, then hydrochloric acid is added to adjust pH to 4-5, afterwards, phase separation is performed again, an organic layer is separated and concentrated to obtain a light-yellow crude product, which is then recrystallized by an organic solvent and dried to obtain a white solid as the final product (i.e., Broflanilide or Cyprofluoranilide). The organic solvent used for the recrystallization is one or a combination of at least two selected from the group consisting of dichloromethane, 1,2-dichloroethane, chloroform, carbon tetrachloride, toluene, xylene, ethyl acetate, methanol, ethanol, and isopropanol, preferably toluene, methanol, or isopropanol.

Compared with the related technics, the present disclosure has the following beneficial effects:

In the preparation method of the present disclosure, a few steps are almost quantitative with few by-products, and deep cooling and high-temperature reactions are not used; furthermore the introduction of bromine atoms at specific sites can be achieved in the final step, and the yield is high, which is more suitable for industrial production. Moreover, the method needs no separation after each preparation step, or the purification can be carried out by using different solvents to obtain high-quality final products.

DETAILED DESCRIPTION

The technical embodiments of the present disclosure will be further described below by way of specific embodiments. It will be apparent to those skilled in the art that the embodiments are merely illustrations of the present disclosure and should not be construed as specific limitations to the present disclosure. The content or purity of the product or intermediate described in the present disclosure and the following examples is measured by HPLC external standard method, and the yield is by mass.

In the present disclosure, the raw material 4-(perfluoropropane-2-yl)-2-(trifluoromethyl)aniline (i.e., decafluoroaniline) is prepared by using a preparation method in the related technics, for example, a preparation method disclosed in EP2319830A1 is used, and the specific preparation method is as follows:

100 g (0.608 mol) of 2-(trifluoromethyl) aniline, 131 g (0.639 mol) of 85% sodium dithionite and 20.9 g (0.0608 mol) of tetrabutylammonium hydrogen sulfate are added to a mixed solution of 1500 ml of ethyl acetate and 1500 ml of water, then 53.9 g (0.639 mol) of sodium bicarbonate is added thereto. 198 g (0.669 mol) of heptafluoroisopropyl iodide is dropwise added thereto at room temperature and stirred at room temperature for 6 hours, then subjected to phase separation, followed by evaporation of solvent of the organic layer under reduced pressure, then 500 ml of ethyl acetate is added thereto. 160 g (0.608 mol) of 4M hydrogen chloride/ethyl acetate solution is dropwise added, followed by stirring at room temperature for 30 minutes and then stirring at 5° C. for 1 h. After filtration, the filtrate is washed with water and a saturated aqueous sodium bicarbonate solution successively, dried over anhydrous magnesium sulfate, and then evaporated under reduced pressure to remove solvents. The obtained residue is purified through silica gel column chromatography (eluting solvent of hexane:ethyl acetate=10:1) to prepare 60.0 g (yield 30%) of 4-(perfluoropropane-2-yl)-2-(trifluoromethyl)aniline.

The overall synthetic route of the present disclosure is as follows:

wherein, $R_1$ is methyl or

$R_2$ is hydrogen or fluorine.

Example 1

In this example, the preparation method for preparing a product where $R_1$ is a methyl group and $R_2$ is a hydrogen, that is,

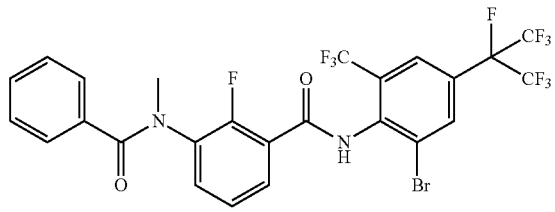 [SMILES: CN(C(=O)c1ccccc1)c1cccc(C(=O)Nc2c(Br)cc(C(F)(C(F)(F)F)C(F)(F)F)cc2C(F)(F)F)c1F]

(Broflanilide) includes the following steps:

(1) Into a 250 mL reactor, 39.6 g (0.21 mol) of 2-fluoro-3-nitrobenzoic acid, 79.2 g of toluene, 31.5 g (0.105 mol) of triphosgene, and 4 drops of DMF were added sequentially, heated to 110° C. and stirred for 6 h until the benzoic acid was converted completely, then the solvent was removed. 67.1 g (0.2 mol) of decafluoroaniline, 0.2 g of DMAP, and 134.2 g of toluene were added sequentially, heated to 110° C. and stirred for 6 hours, then 40 g of 10% sodium carbonate solution was added slowly after slightly cooling, stirred at 80° C. for 30 min, followed by phase separation while it was hot. The organic layer was cooled to room temperature, placed in water chiller at 0° C. for 3 h, filtered and dried to obtain 96.2 g of nitroamide as a yellow solid in purity 98.4% and yield 95.4%.

Characterization data: LC/MS[M+1]: m/z=497;

$^1$H NMR (400 MHz, DMSO-$d_6$) (δ[ppm]): 10.74 (s, 1H), 8.35 (t, J=8.5 Hz, 1H), 8.20-8.03 (m, 3H), 7.96 (s, 1H), 7.62 (t, J=8.0 Hz, 1H).

(2) Into a 1 L autoclave, 99.2 g (0.2 mol) of nitroamide, 0.49 g of 10% platinum-carbon catalyst, and 496 g of ethyl acetate were added sequentially. Hydrogen was charged to a pressure of 2.3 MPa, stirred at 40° C. for 14 h and filtered.

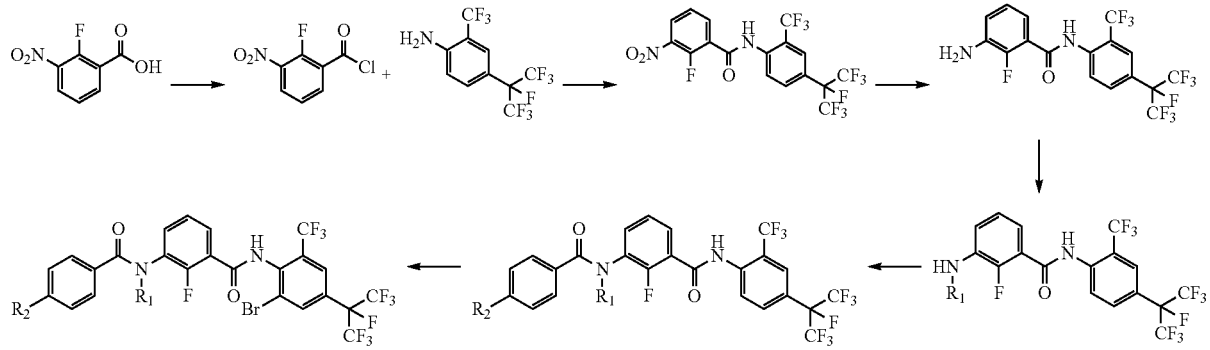

The filtrate was concentrated to obtain a caesious solid, which was dried to obtain 93.5 g of aminoamide in purity 98.8% and yield 99.1%.

Characterization data: LC/MS[M+1]: m/z=467;

$^1$H NMR (400 MHz, DMSO-$d_6$) (δ[ppm]): 10.14 (s, 1H), 8.16-8.03 (m, 2H), 7.93 (s, 1H), 7.07-6.92 (m, 2H), 6.86 (t, J=5.8 Hz, 1H), 5.43 (s, 2H).

(3) Into a 500 mL reactor, 190 g of concentrated sulfuric acid, 47.5 g (0.1 mol) of aminoamide, 32.4 g (0.4 mol) of 37% formaldehyde were added sequentially, heated to 50° C. and stirred for 18 h. After the completion of the reaction, the mixture were poured into 500 g of ice-water, stirred at room temperature for 2 h and filtered. The filter cake was washed with 200 g of water and dried to obtain 45.1 g of methylaminoamide as a white solid in purity 98.0% and yield 92.1%.

Characterization data: LC/MS[M+1]: m/z=481;

$^1$H NMR (400 MHz, DMSO-$d_6$) (δ[ppm]): δ 10.17 (d, J=3.7 Hz, 1H), 8.12-8.07 (m, 2H), 7.92 (s, 1H), 7.14 (t, J=7.9 Hz, 1H), 6.91-6.83 (m, 2H), 5.89 (bro-s, 1H), 2.78 (d, J=4.8 Hz, 3H).

(4) Into a 500 mL reactor, 48.9 g (0.1 mol) of methyl-aminoamide, 0.2 g of DMAP, 195.6 g of 1,2-dichloroethane, and 15.1 g (0.105 mol) of benzoyl chloride were added sequentially, heated to 80° C. and stirred for 5 h. 40 g of 10% sodium carbonate solution was added slowly, stirred at 80° C. for 30 min. While the mixture was hot, phase separation was carried out to obtain 255.8 g of organic phase to be used for next step, wherein the content of Broflanilide diamide was 22.6%, and the yield was 99.0%.

Characterization data: LC/MS[M+1]: m/z=585;

$^1$H NMR (400 MHz, DMSO-$d_6$) (δ[ppm]): δ 10.34 (s, 1H), 8.11 (dd, J=8.7, 2.1 Hz, 1H), 8.01 (d, J=8.6 Hz, 1H), 7.93 (d, J=2.2 Hz, 1H), 7.62-7.58 (m, J=5.8, 2H), 7.36-7.27 (m, 6H), 3.36 (s, 3H).

(5) Into a 500 mL reactor, 255.8 g (purity 22.6%, 0.0992 mol) of organic phase obtained in step (4), 12.3 g (0.119 mol) of sodium bromide, 2.1 g (0.0496 mol) of NaOH, and 30 g of water were added sequentially, heated to 40° C., then 21.3 g of 20% sodium chlorate solution was dropwise added, after the dropwise addition, the reaction was continued for 1.5 h, then subjected to phase separation while it was hot, the organic phase was washed with 50 g of a 7.5% sodium sulfite solution at 50° C., the pH of which is adjusted to 4 with 11.6 g of concentrated hydrochloric acid, and then subjected to phase separation while it was hot, the organic phase was concentrated to obtain 68.9 g of a pale yellow crude product which was dissolved in 60 mL of methanol for recrystallization, dried to obtain 61.1 g of product as a white solid (i.e. Broflanilide) in purity 99.4% and yield 92.3%.

Characterization data: LC/MS[M+1]: m/z=664;

$^1$H NMR (400 MHz, DMSO-$d_6$) (δ[ppm]): δ 10.69 (s, 1H), 8.41 (s, 1H), 7.96 (s, 1H), 7.63-7.57 (m, 2H), 7.36-7.28 (m, 6H), 3.37 (s, 3H).

Example 2

In this example, the preparation method for preparing a product where $R_1$ is a methyl group and $R_2$ is a hydrogen, that is,

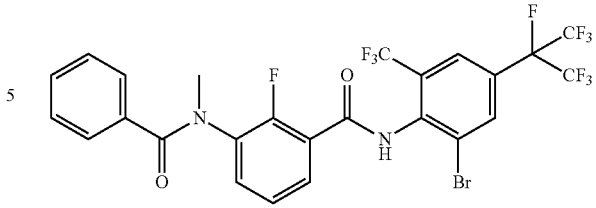

(Broflanilide) includes the following steps:

(1) Into a 500 mL reactor, 45.3 g (0.24 mol) of 2-fluoro-3-nitrobenzoic acid, 136 g of xylene, 42.9 g (0.36 mol) of thionyl chloride, and 4 drops of DMF were added sequentially, heated to 140° C. and stirred for 5 h until benzoic acid was converted completely. Solvent was removed. 67.1 g (0.2 mol) of decafluoroaniline, 0.2 g of DMAP, and 201.3 g of xylene were added sequentially, heated to 140° C. and stirred for 4 hours. 40 g of 10% sodium hydroxide solution was added slowly after slightly cooling and stirred at 80° C. for 30 min. While the mixture was hot, phase separation was carried out to obtain organic layer. The organic layer was cooled to room temperature, placed in a water chiller at 5° C. for 3 h, filtered and dried to obtain 96.6 g of nitroamide as a yellow solid in purity 98.6% and yield 96.0%.

(2) Into a 1 L autoclave, 99.2 g (0.2 mol) of nitroamide, 0.59 g of 10% palladium-carbon catalyst, and 595.2 g of methanol were added sequentially. Hydrogen was charged to a pressure of 2.5 MPa, stirred at 60° C. for 12 h and filtered. The filtrate was concentrated to obtain a caesious solid which was dried to obtain 93.3 g of aminoamide in purity 98.9% and yield 99.0%.

(3) Into a 500 mL reactor, 237.5 g of concentrated sulfuric acid, 47.5 g (0.1 mol) of aminoamide, 40.5 g (0.5 mol) of 37% formaldehyde were added sequentially, heated to 65° C. and stirred for 16 h. After the completion of the reaction, the mixture was poured into 500 g of ice-water, stirred at room temperature for 2 h and filtered. The filter cake was washed with 200 g of water and dried to obtain 46.3 g of methylaminoamide as a white solid in purity 97.5% and yield 94.0%.

(4) Into a 500 mL reactor, 48.9 g (0.1 mol) of methyl-aminoamide, 0.2 g of DMAP, 244.5 g of toluene, and 15.5 g (0.108 mol) of benzoyl chloride were added sequentially, heated to 100° C. and stirred for 4 h. 40 g of 10% sodium hydroxide solution was slowly added and stirred at 80° C. for 30 min. While the mixture was hot, phase separation was carried out to obtain 304.2 g of organic phase to be used for next step, wherein the content of Broflanilide diamide was 19.0%, and the yield was 99.0%.

(5) Into a 500 mL reactor, 304.2 g (purity 19.0%, 0.099 mol) of the organic phase obtained in step (4), 28 g (0.14 mol) of 40% hydrobromic acid, 30 g of water and 7.5 g (0.18 mol) of NaOH were added sequentially and heated to 70° C. 82.2 g of 14.5% sodium hypochlorite solution was dropwise added and the reaction was continued for 1 h after the dropwise addition. While the mixture was hot, phase separation was carried out. The organic phase was washed with 50 g of a 7.5% sodium sulfite solution at 70° C., and adjusted to pH=5 with 12.5 g of concentrated hydrochloric acid. The mixture was subjected to phase separation while it was hot, the organic phase was concentrated to obtain 68.5 g of a pale yellow crude product, which was dissolved in 90 mL of toluene, recrystallized, filtered and dried to obtain 60.6 g of product as a white solid (i.e. Broflanilide) in purity 99.1% and yield 91.5%.

Example 3

In this example, the preparation method for preparing a product where $R_1$ is a methyl group and $R_2$ is a hydrogen, that is,

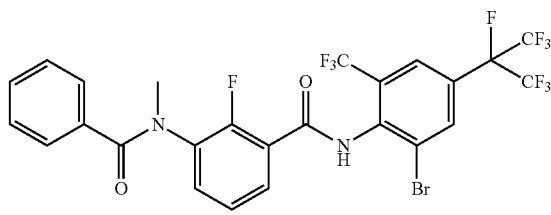 [SMILES: CN(C(=O)c1ccccc1)c1cccc(C(=O)Nc2c(Br)cc(C(F)(C(F)(F)F)C(F)(F)F)cc2C(F)(F)F)c1F]

(Broflanilide) includes the following steps:

(1) Into a 500 mL reactor, 49.1 g (0.26 mol) of 2-fluoro-3-nitrobenzoic acid, 196.4 g of toluene, 61.9 g (0.52 mol) of thionyl chloride, and 4 drops of DMF were added sequentially, heated to 110° C. and stirred for 4 h until benzoic acid was converted completely. The solvent was removed. 67.1 g (0.2 mol) of decafluoroaniline, 0.2 g of DMAP, and 268.4 g of toluene were added sequentially, heated to 110° C. and stirred for 5 hours. 40 g of 10% sodium carbonate solution was added slowly after slightly cooling, stirred at 80° C. for 30 min, then subjected to phase separation while it was hot to obtain 368.8 g of organic layer in a nitroamide content of 26.5% and yield 98.4%.

(2) Into a 1 L autoclave, 368.8 g of the organic layer obtained in step (1) and 0.29 g of 10% palladium-carbon catalyst were charged. Hydrogen was charged to a pressure of 2.0 MPa, stirred at 100° C. for 10 h and filtered. The filtrate was dried to obtain 288.4 g of aminoamide toluene solution in aminoamide content of 31.5% and yield 99.0%.

(3) Into a 500 mL reactor, 285 g of concentrated sulfuric acid, 47.5 g (0.1 mol) of aminoamide, 48.6 g (0.6 mol) of 37% formaldehyde were added sequentially, heated to 80° C. and stirred for 14 h. After the completion of the reaction, the mixture was poured into 500 g of ice-water, stirred at room temperature for 2 h and filtered. The filter cake was washed with 200 g of water and dried to obtain 45.8 g of methylaminoamide as an off-white solid in purity 97.3% and yield 92.8%.

(4) Into a 500 mL reactor, 48.9 g (0.1 mol) of methylaminoamide, 0.2 g of DMAP, 293.4 g of toluene, and 15.8 g (0.11 mol) of benzoyl chloride were added sequentially, heated to 110° C. and stirred for 3 h. 40 g of 10% sodium carbonate solution was slowly added and stirred at 80° C. for 30 min. Phase separation was carried out while the mixture was hot to obtain 355.1 g of organic phase to be used for next step, wherein the content of Broflanilide diamide was 16.3% and the yield was 99.3%.

(5) Into a 500 mL reactor, 355.1 g (purity 16.3%, 0.0993 mol) of the organic phase obtained in step (4), 16.6 g (0.16 mol) of sodium bromide, 30 g of water, and 18.5 g (0.28 mol) of KOH were added sequentially and heated to 90° C. 8.5 g (0.12 mol) of chlorine gas was slowly introduced. The reaction was continued for 2 h and subjected to phase separation while it was hot. The organic phase was washed with 50 g of a 7.5% sodium sulfite solution at 90° C. and adjusted to pH=4.5 with 13.2 g of concentrated hydrochloric acid. Phase separation was carried out while the mixture was hot. The organic phase was concentrated to obtain 67.6 g of a pale yellow crude product, which was dissolved in 60 mL of isopropanol, recrystallized, filtered and dried to obtain 61.8 g of product as a white solid (i.e. Broflanilide) in purity 99.3% and yield 93.2%.

Examples 2 and 3 were also subjected to the same mass spectrometry and nuclear magnetic resonance characterization as Example 1. The structure of the product was verified to be correct.

Example 4

In this example, the preparation method for preparing a product where $R_1$ is cylopropylmethyl group and $R_2$ is fluoro, that is,

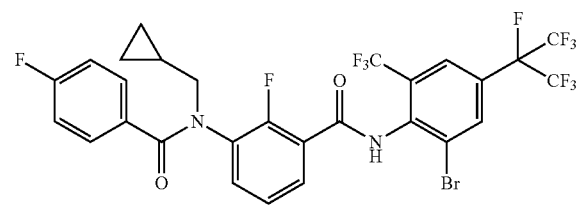 [SMILES: O=C(Nc1c(Br)cc(C(F)(C(F)(F)F)C(F)(F)F)cc1C(F)(F)F)c1cccc(N(CC2CC2)C(=O)c2ccc(F)cc2)c1F]

(Cyprofluoranilide) includes the following steps:

(1) Into a 500 mL reactor, 49.1 g (0.26 mol) of 2-fluoro-3-nitrobenzoic acid, 196.4 g of toluene, 61.9 g (0.52 mol) of thionyl chloride, and 4 drops of DMF were added sequentially, heated to 110° C. and stirred for 4 h until benzoic acid was converted completely. The solvent was removed. 67.1 g (0.2 mol) of decafluoroaniline, 0.2 g of DMAP, and 268.4 g of toluene were added sequentially, heated to 110° C. and stirred for 5 hours. 40 g of 10% sodium carbonate solution was added slowly after slightly cooling, stirred at 80° C. for 30 min, then subjected to phase separation while it was hot to obtain 368.8 g of organic layer in a nitroamide content of 26.5% and yield 98.4%.

(2) Into a 1 L autoclave, 368.8 g of the organic layer obtained in step (1) and 0.29 g of a 10% palladium-carbon catalyst were charged. Hydrogen was charged to a pressure of 2.0 MPa stirred at 100° C. for 10 h and filtered. The filtrate was dried to obtain 360.4 g of aminoamide toluene solution in aminoamide content of 25.2% and yield 99.0%.

(3) Into a 500 mL reactor, 360.4 g (purity 25.2%, 0.196 mol) of the aminoamide toluene solution obtained in step (2), 22.4 g (0.31 mol) of cyclopropanecarboxaldehyde, and 25.5 g (0.392 mol) of zinc powder were added sequentially. 47.1 g (0.784 mol) of acetic acid was dropwise added at 60° C., after the dropwise addition and the reaction was continued for 2 h. The mixture was filtered while it was hot. The filtrate was adjusted to pH=7 with 160 g of 20% sodium hydroxide solution at 50° C. and subjected to phase separation while it was hot to obtain 381.1 g of the cyclopropylaminoamide toluene solution in cyclopropylaminoamide content of 25.6% and yield 95.6%.

Characterization data: LC/MS[M+1]: m/z=521;

$^1$H NMR (400 MHz, DMSO-d$_6$) (δ[ppm]): 10.18 (s, 1H), 8.12-8.07 (m, 1H), 8.04 (d, J=8.7 Hz, 1H), 7.92 (s, 1H), 7.10 (t, J=7.9 Hz, 1H), 6.94 (t, J=8.2 Hz, 1H), 6.90-6.82 (m, 1H), 5.82-5.72 (m, 1H), 3.03 (t, J=6.2 Hz, 2H), 1.12-1.08 (m, 1H), 0.50-0.42 (m, 2H), 0.24 (q, J=4.4 Hz, 2H).

(4) Into a 500 mL reactor, 53.1 g (0.1 mol) of cyclopropylaminoamide, 0.2 g of DMAP, 265.5 g of 1-dichloroethane, and 17.0 g (0.105 mol) of 4-fluorobenzoyl chloride were added sequentially, heated to 80° C. and stirred for 4 h. 40 g of 10% sodium carbonate solution was slowly added and stirred at 80° C. for 30 min. Phase separation was carried out while it was hot to obtain 332.9 g of organic phase to be used for next step, wherein the content of Cyprofluoranilide diamide was 19.1% and the yield was 99.0%.

Characterization data: LC/MS[M+1]: m/z=643;

$^1$H NMR (400 MHz, DMSO-$d_6$) (δ[ppm]): 10.21 (s, 1H), 8.09 (d, J=8.0 Hz, 1H), 7.99 (d, J=8.0 Hz, 1H), 7.92 (s, 1H), 7.61-7.59 (m, 2H), 7.36-7.22 (m, 6H), 3.68 (d, J=52.0 Hz, 2H), 1.02 (brs, 1H), 0.40 (d, J=8.0 Hz, 2H), 0.08 (brs, 2H).

(5) Into a 500 mL reactor, 332.9 g (purity 19.1%, 0.099 mol) of organic phase obtained in step (4), 12.3 g (0.119 mol) of sodium bromide, 2.1 g (0.049 mol) of NaOH, and 30 g of water were added sequentially and heated to 40° C. 21.3 g of a 20% sodium chlorate solution was dropwise added, after the dropwise addition, the reaction was continued for 1.5 h. Phase separation was carried out while it was hot. The organic phase was washed with 50 g of 7.5% sodium sulfite solution at 50° C. and adjusted to pH=4 with 11.9 g of concentrated hydrochloric acid. Phase separation was carried out while the mixture was hot. The organic phase was concentrated to obtain 74.8 g of a pale yellow crude product, which was dissolved in 60 mL of methanol, recrystallized, filtered and dried to obtain 66.7 g of Cyprofluoranilide diamide product as a white solid in purity 99.4% and yield 92.9%.

Characterization data: LC/MS[M+1]: m/z=722;

$^1$H NMR (400 MHz, DMSO-$d_6$) (δ[ppm]): 10.56 (s, 1H), 8.41 (s, 1H), 7.95 (s, 1H), 7.70-7.56 (m, 2H), 7.38-7.32 (m, 3H), 7.09 (br s, 2H), 3.69 (br s, 2H), 1.03-1.01 (m, 1H), 0.41-0.39 (m, 2H), 0.08-0.06 (m, 2H).

Example 5

In this example, the preparation method for preparing a product where $R_1$ is cylopropylmethyl group and $R_2$ is fluoro, that is,

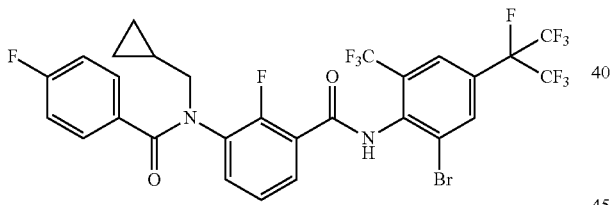

(Cyprofluoranilide) includes the following steps:

(1) Into a 500 mL reactor, 49.1 g (0.26 mol) of 2-fluoro-3-nitrobenzoic acid, 196.4 g of toluene, 61.9 g (0.52 mol) of thionyl chloride, and 4 drops of DMF were added sequentially, heated to 110° C. and stirred for 4 h until benzoic acid was converted completely. The solvent is removed. 67.1 g (0.2 mol) of decafluoroaniline, 0.2 g of DMAP, and 268.4 g of toluene were added sequentially, heated to 110° C. and stirred for 5 hours. 40 g of 10% sodium carbonate solution was added slowly after slightly cooling and stirred at 80° C. for 30 min. Phase separation was carried out while the mixture was hot to obtain 368.8 g of organic layer in a nitroamide content of 26.5% and yield 98.4%.

(2) Into a 1 L autoclave, 368.8 g of the organic layer obtained in step (1) and 0.29 g of a 10% palladium-carbon catalyst were charged. Hydrogen was charged to a pressure of 2.0 MPa stirred at 100° C. for 10 h and filtered. The filtrate was dried to obtain 360.4 g of aminoamide toluene solution in aminoamide content of 25.2% and yield 99.0%.

(3) Into a 500 mL reactor, 360.4 g (purity 25.2%, 0.196 mol) of the aminoamide toluene solution obtained in step (2), 22.4 g (0.31 mol) of cyclopropanecarboxaldehyde, and 25.5 g (0.392 mol) of zinc powder were added sequentially. 47.1 g (0.784 mol) of acetic acid was dropwise added at 60° C., after the dropwise addition, the reaction was continued for 2 h. Phase separation was carried out while the mixture was hot. The filtrate was adjusted to pH=8 with 160 g of 20% sodium hydroxide solution at 50° C. and subjected to phase separation while it was hot to obtain 381.1 g of the cyclopropylaminoamide toluene solution in cyclopropylaminoamide content of 25.6%, and yield 95.6%.

(4) Into a 500 mL reactor, 381.1 g (purity 25.6%, 0.187 mol) of cyclopropylaminoamide toluene solution obtained in step (3), 0.2 g of DMAP, and 34.0 g (0.21 mol) of 4-fluorobenzoyl chloride were added sequentially, heated to 100° C. and stirred for 4 h. 40 g of a 20% sodium hydroxide solution was slowly added and stirred at 80° C. for 30 min. Phase separation was carried out while the mixture was hot to obtain 404.8 g of organic phase to be used for next step, wherein the content of Cyprofluoranilide diamide was 29.3% and the yield was 98.8%.

(5) Into a 500 mL reactor, 404.8 g (purity 29.3%, 0.187 mol) of the organic phase obtained in step (4), 53.6 g (0.265 mol) of 40% hydrobromic acid, 30 g of water and 14.2 g (0.34 mol) of NaOH were added sequentially and heated to 70° C. 155.4 g of 14.5% sodium chlorate solution was dropwise added, after the dropwise addition, the reaction was continued for 1 h. Phase separation was carried out while it was hot. The organic phase was washed with 50 g of 7.5% sodium sulfite solution at 70° C., adjusted to pH=5 with 12.9 g of concentrated hydrochloric acid, and subjected to phase separation while it was hot. The organic phase was concentrated to obtain 138.7 g of a pale yellow crude product, which was dissolved in 180 mL of toluene, recrystallized, filtered, and dried to obtain 123.0 g of Cyprofluoranilide diamide product as a white solid in purity 99.2% and yield 90.5%.

Example 6

In this example, the preparation method for preparing a product where $R_1$ is cylopropylmethyl group and $R_2$ is fluoro, that is,

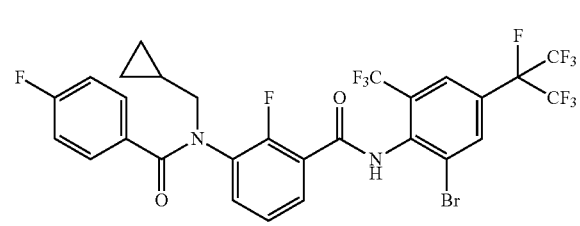 [SMILES: O=C(Nc1c(Br)cc(C(F)(C(F)(F)F)C(F)(F)F)cc1C(F)(F)F)c1cccc(N(CC2CC2)C(=O)c2ccc(F)cc2)c1F]

(Cyprofluoranilide) includes the following steps:

(1) Into a 500 mL reactor, 49.1 g (0.26 mol) of 2-fluoro-3-nitrobenzoic acid, 196.4 g of toluene, 61.9 g (0.52 mol) of thionyl chloride, and 4 drops of DMF were added sequentially, heated to 110° C. and stirred for 4 h until benzoic acid was converted completely. The solvent was removed. 67.1 g (0.2 mol) of decafluoroaniline, 0.2 g of DMAP, and 268.4 g of toluene were added sequentially, heated to 110° C. and stirred for 5 hours. 40 g of 10% sodium carbonate solution was added slowly after slightly cooling, stirred at 80° C. for 30 min. Phase separation was carried out while the mixture was hot to obtain 368.8 g of organic layer in nitroamide content of 26.5% and yield 98.4%.

(2) Into a 1 L autoclave, 368.8 g of the organic layer obtained in step (1) and 0.29 g of a 10% palladium-carbon catalyst were added. Hydrogen was charged to a pressure of 2.0 MPa, stirred at 100° C. for 10 h and filtered. The filtrate was dried to obtain 360.4 g of aminoamide toluene solution in aminoamide content of 25.2% and yield 99.0%.

(3) Into a 500 mL reactor, 47.5 g (0.1 mol) of aminoamide, 285 g of xylene, 14.3 g (0.2 mol) of cyclopropanecarboxaldehyde, and 26 g (0.4 mol) of zinc powder were added sequentially. 48 g (0.6 mol) of acetic acid was dropwise added when the temperature reached 80° C., after the dropwise addition, the reaction was continued for 1.5 h and filtered while it was hot. The filtrate was concentrated to obtain a yellow solid, which was dissolved completely in 50 mL of toluene at 90° C., followed by addition of 50 mL of water. The mixture was adjusted to pH=7.5 by 5.9 g of 30% sodium hydroxide solution and subjected to phase separation while it was hot. The organic layer was stirred at 0° C. for 3 h, filtered, concentrated and dried to obtain 50.8 g of a pale yellow solid in purity 98.7% and yield 96.4%.

(4) Into a 500 mL reactor, 53.1 g (0.1 mol) of cyclopropylaminoamide, 0.2 g of DMAP, 318.6 g of toluene, and 17.8 g (0.11 mol) of 4-fluorobenzoyl chloride were added sequentially, heated to 110° C. and stirred for 3 h. 40 g of 10% sodium carbonate solution was slowly added, stirred at 80° C. for 30 min, and subjected to phase separation while it was hot to obtain 385.9 g of organic phase to be used for next step, wherein the content of Cyprofluoranilide diamide was 16.5% and the yield was 99.2%.

(5) Into a 500 mL reactor, 385.9 g (purity 16.5%, 0.0992 mol) of the organic phase obtained in step (4), 16.3 g (0.158 mol) of sodium bromide, 30 g of water, and 18.3 g (0.277 mol) of KOH were added sequentially and heated to 90° C. 8.5 g (0.119 mol) of chlorine gas was charged, after that, the reaction was continued for 2 h. Phase separation was carried out while the mixture was hot. The organic phase was washed with 50 g of 7.5% sodium sulfite solution at 90° C., adjusted to pH=4 with 13.8 g of concentrated hydrochloric acid, and subjected to phase separation while it was hot. The organic phase was concentrated to obtain 73.5 g of a pale yellow crude product, which was dissolved in 90 mL of isopropanol, recrystallized, filtered and dried to obtain 67.1 g of product Cyprofluoranilide as a white solid in purity 99.3% and yield 93.2%.

Examples 5 and 6 were also subjected to the same mass spectrometry and nuclear magnetic resonance characterization as Example 4, and the structure of the product was verified to be correct.

Applicant has stated that although the preparation method for m-diamide compounds of the present disclosure has been described by the above Examples in the present disclosure, the present disclosure is not limited thereto, that is to say, it is not meant that the present disclosure has to be implemented depending on the above Examples. It will be apparent to those skilled in the art that any improvements made to the present disclosure, equivalent replacements and addition of adjuvant ingredients to the raw materials of the products of the present disclosure, and selections of the specific implementations, etc., all fall within the protection scope and the disclosed scope of the present disclosure.

What is claimed is:

1. A preparation method for m-diamide compounds having a structure of formula I, wherein the preparation method comprises the following steps:
   (1) 2-fluoro-3-nitrobenzoyl chloride and 4-(perfluoropropane-2-yl)-2-(trifluoromethyl) aniline are subjected to a condensation reaction to give 2-fluoro-3-nitro-N-(4-(perfluoropropane-2-yl)-2-(trifluoromethyl) phenyl) benzamide, the reaction scheme is as follows:

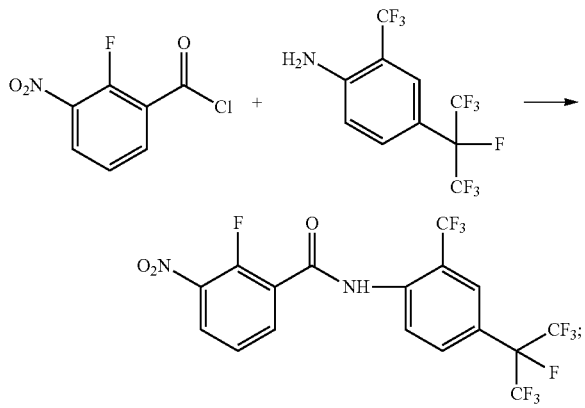

(2) 2-fluoro-3-nitro-N-(4-(perfluoropropane-2-yl)-2-(trifluoromethyl) phenyl) benzamide is subjected to a reduction reaction to give 3-amino-2-fluoro-N-(4-(perfluoropropane-2-yl)-2-(trifluoromethyl) phenyl) benzamide, the reaction scheme is as follows:

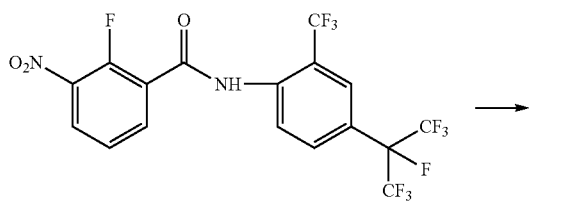

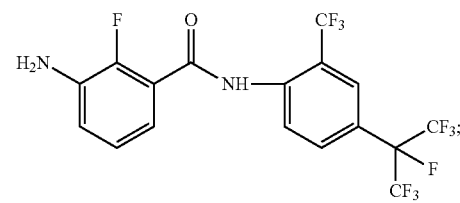

(3) 3-amino-2-fluoro-N-(4-(perfluoropropane-2-yl)-2-(trifluoromethyl) phenyl)benzamide and an alkylating agent are subjected to an alkylation reaction to give 2-fluoro-3-(alkylamino)-N-(4-(perfluoropropane-2-yl)-2-(trifluoromethyl)phenyl)benzamide, the reaction scheme is as follows:

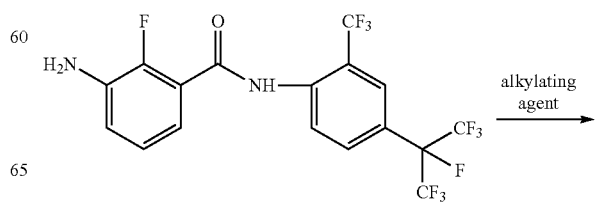

-continued

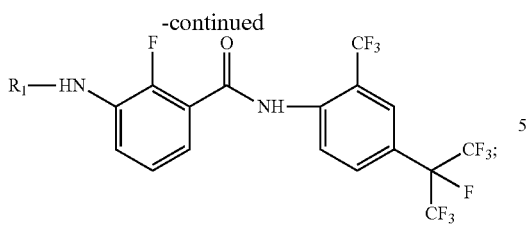

(4) 2-fluoro-3-(alkylamino)-N-(4-(perfluoropropane-2-yl)-2-(trifluoromethyl)phenyl)benzamide reacts acyl chloride compound represented by formula II to give 2-fluoro-3-(alkylbenzamido)-N-(4-(perfluoropropane-2-yl)-2-(trifluoromethyl)phenyl)benzamide, and the reaction scheme is as follows:

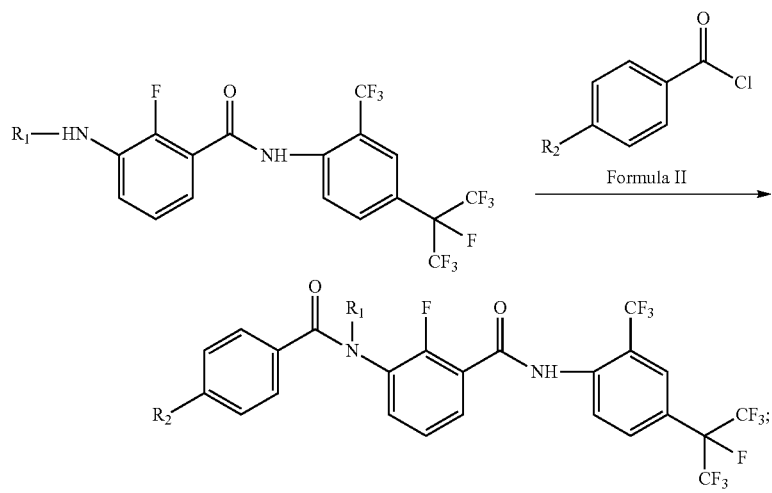

(5) 2-fluoro-3-(alkylbenzamido)-N-(4-(perfluoropropane-2-yl)-2-(trifluoromethyl)phenyl) benzamide is brominated to give the m-diamide compound represented by formula I, and the reaction scheme is as follows:

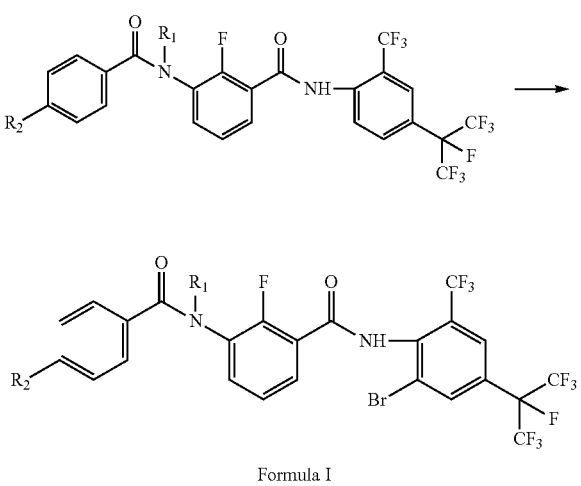

Formula I wherein, $R_1$ is methyl or

$R_2$ is hydrogen or fluorine.

2. The preparation method according to claim 1, wherein 2-fluoro-3-nitrobenzoyl chloride in step (1) can be prepared by the following method: A) 2-fluoro-3-nitrobenzoic acid is reacted with an acyl chlorinating reagent to give 2-fluoro-3-nitrobenzoyl chloride.

3. The preparation method according to claim 2, wherein the acyl chlorinating reagent in step A is one or a combination of at least two selected from the group consisting of thionyl chloride, triphosgene, oxalyl chloride, phosphorus trichloride, and phosphorus pentachloride;
wherein the molar ratio of 2-fluoro-3-nitrobenzoic acid to the acyl chlorinating reagent in step A is 1:0.33 to 1:2.5;
wherein the solvent of the reaction in step A is any one or a combination of at least two selected from the group consisting of dichloromethane, 1,2-dichloroethane, chloroform, benzene, toluene, xylene, chlorobenzene, and dichlorobenzene;
wherein mass ratio of 2-fluoro-3-nitrobenzoic acid to the solvent in step A is 1:1 to 1:5;
wherein the temperature of the reaction in step A is 40-180° C.;
wherein the reaction time in step A is 3-8 h.

4. The preparation method according to claim 3, wherein the acyl chlorinating reagent in step A is thionyl chloride or triphosgene;
wherein the molar ratio of 2-fluoro-3-nitrobenzoic acid to the acyl chlorinating reagent in step A is 1:0.5 to 1:2.0;
wherein the solvent of the reaction in step A is toluene and/or xylene;
wherein mass ratio of 2-fluoro-3-nitrobenzoic acid to the solvent in step A is 1:2 to 1:4;
wherein the temperature of the reaction in step A is 110-140° C.;
wherein the reaction time in step A is 4-6 h.

5. The preparation method according to claim 1, wherein in step (1), molar ratio of 2-fluoro-3-nitrobenzoyl chloride to 4-(perfluoropropane-2-yl)-2-(trifluoromethyl) aniline is 1:1 to 1.5:1;
wherein the solvent of the reaction in step (1) is any one or a combination of at least two selected from the group consisting of dichloromethane, 1,2-dichloroethane, chloroform, benzene, toluene, xylene, chlorobenzene, and dichlorobenzene;
wherein mass ratio of 4-(perfluoropropane-2-yl)-2-(trifluoromethyl) aniline to the solvent in step (1) is 1:1-1:5;
wherein the reaction in step (1) is performed in the presence of a catalyst, and the catalyst is 4-dimethylaminopyridine;
wherein the used amount of the catalyst is 0.1%-5% by mass of 4-(perfluoropropane-2-yl)-2-(trifluoromethyl) aniline.

6. The preparation method according to claim 5, wherein after the reaction in step (1) is completed, post-treatment is performed, and the post-treatment includes the following steps:
an alkali solution is added to the reaction system, stirred at 80° C. for 10-40 min, and subjected to phase separation while it is hot, the resulting organic layer is cooled to room temperature, then stirred at 0-5° C. for 1-3 h, filtered and dried to give 2-fluoro-3-nitro-N-(4-(perfluoropropane-2-yl)-2-(trifluoromethyl) phenyl) benzamide; wherein the alkali solution is one or a combination of at least two selected from the group consisting of aqueous solution of hydroxide, carbonate or bicarbonate of an alkali metal or an alkaline earth metal.

7. The preparation method according to claim 6, wherein the alkali solution is a sodium hydroxide solution or a sodium carbonate solution.

8. The preparation method according to claim 5, wherein in step (1), molar ratio of 2-fluoro-3-nitrobenzoyl chloride to 4-(perfluoropropane-2-yl)-2-(trifluoromethyl) aniline is 1.1:1 to 1.3:1;
wherein the solvent of the reaction in step (1) is toluene and/or xylene;
wherein mass ratio of 4-(perfluoropropane-2-yl)-2-(trifluoromethyl) aniline to the solvent in step (1) is 1:2-1:4.

9. The preparation method according to claim 1, wherein the temperature of the condensation reaction in step (1) is 40-180° C.;
wherein the time of the condensation reaction in step (1) is 3-8 h.

10. The preparation method according to claim 1, wherein the catalyst for the reduction reaction in step (2) is any one selected from the group consisting of palladium-carbon, platinum-carbon, and Raney nickel;
wherein content of active substance in the catalyst is not less than 10%;
wherein in step (2), mass ratio of 2-fluoro-3-nitro-N-(4-(perfluoropropane-2-yl)-2-(trifluoromethyl) phenyl) benzamide to the catalyst is 1:0.001 to 1:0.01;
wherein the reductant of the reduction reaction in step (2) is hydrogen;
wherein in the reduction reaction in step (2), the pressure after introducing hydrogen is controlled to be 1.5-3.0 MPa;
wherein the temperature of the reduction reaction in step (2) is 25-120° C.;
wherein the time of the reduction reaction in step (2) is 8-16 h.

11. The preparation method according to claim 10, wherein the catalyst for the reduction reaction in step (2) is palladium-carbon or platinum-carbon catalyst;
wherein content of active substance in the catalyst is 10% palladium-carbon catalyst;
wherein in step (2), mass ratio of 2-fluoro-3-nitro-N-(4-(perfluoropropane-2-yl)-2-(trifluoromethyl) phenyl) benzamide to the catalyst is 1:0.003 to 1:0.006;
wherein in the reduction reaction in step (2), the pressure after introducing hydrogen is controlled to be 2.0-2.5 MPa;
wherein the temperature of the reduction reaction in step (2) is 40-100° C.;
wherein the time of the reduction reaction in step (2) is 10-14 h.

12. The preparation method according to claim 1, wherein the alkylating agent in step (3) is formaldehyde or cyclopropanecarboxaldehyde;
wherein when the alkylating agent in step (3) is formaldehyde, molar ratio of 3-amino-2-fluoro-N-(4-(perfluoropropane-2-yl)-2-(trifluoromethyl) phenyl) benzamide to formaldehyde is 1:2 to 1:8;
wherein when the alkylating reagent in step (3) is formaldehyde, the alkylation reaction is performed in the presence of concentrated sulfuric acid;
wherein mass ratio of 3-amino-2-fluoro-N-(4-(perfluoropropane-2-yl)-2-(trifluoromethyl) phenyl) benzamide to concentrated sulfuric acid is 1:3 to 1:10;
wherein when the alkylating reagent in step (3) is formaldehyde, the temperature of the alkylation reaction in step (3) is 25-100° C.;
wherein when the alkylating reagent in step (3) is formaldehyde, the time of the alkylation reaction in step (3) is 12-24 h.

13. The preparation method according to claim 12, wherein when the alkylating agent in step (3) is formaldehyde, molar ratio of 3-amino-2-fluoro-N-(4-(perfluoropropane-2-yl)-2-(trifluoromethyl) phenyl) benzamide to formaldehyde is 1:4 to 1:6;
wherein mass ratio of 3-amino-2-fluoro-N-(4-(perfluoropropane-2-yl)-2-(trifluoromethyl) phenyl) benzamide to concentrated sulfuric acid is 1:4 to 1:6;
wherein when the alkylating reagent in step (3) is formaldehyde, the temperature of the alkylation reaction in step (3) is 50-80° C.;
wherein when the alkylating reagent in step (3) is formaldehyde, the time of the alkylation reaction in step (3) is 14-18 h.

14. The preparation method according to claim 1, wherein when the alkylating reagent in step (3) is cyclopropanecarboxaldehyde, the alkylation reaction in step (3) is performed in the presence of zinc powder;
wherein molar ratio of 3-amino-2-fluoro-N-(4-(perfluoropropane-2-yl)-2-(trifluoromethyl) phenyl) benzamide to zinc powder is 1:1.5 to 1:6;
wherein when the alkylating agent in step (3) is cyclopropanecarboxaldehyde, the molar ratio of the 3-amino-2-fluoro-N-(4-(perfluoropropane-2-yl)-2-(trifluoromethyl) phenyl) benzamide to cyclopropanecarboxaldehyde is 1:1.2 to 1:3;
wherein when the alkylating reagent in step (3) is cyclopropanecarboxaldehyde, the alkylation reaction in step (3) is performed in the presence of acetic acid;
wherein molar ratio of 3-amino-2-fluoro-N-(4-(perfluoropropane-2-yl)-2-(trifluoromethyl) phenyl) benzamide to acetic acid is 1:3 to 1:12;

wherein when the alkylating reagent in step (3) is cyclopropanecarboxaldehyde, the temperature of the alkylation reaction is 30-90° C.;

wherein when the alkylating reagent in step (3) is cyclopropanecarboxaldehyde, the time of the alkylation reaction is 1-4 h;

wherein when the alkylating reagent in step (3) is cyclopropanecarboxaldehyde, the solvent of the alkylation reaction is one or a combination of at least two selected from the group consisting of methanol, ethyl acetate, 1,2-dichloroethane, toluene, and xylene.

15. The preparation method according to claim 14, wherein molar ratio of 3-amino-2-fluoro-N-(4-(perfluoropropane-2-yl)-2-(trifluoromethyl) phenyl) benzamide to zinc powder is 1:2 to 1:4;

wherein when the alkylating agent in step (3) is cyclopropanecarboxaldehyde, the molar ratio of the 3-amino-2-fluoro-N-(4-(perfluoropropane-2-yl)-2-(trifluoromethyl) phenyl) benzamide to cyclopropanecarboxaldehyde is 1:1.6 to 1:2;

wherein molar ratio of 3-amino-2-fluoro-N-(4-(perfluoropropane-2-yl)-2-(trifluoromethyl) phenyl) benzamide to acetic acid is 1:4 to 1:8;

wherein when the alkylating reagent in step (3) is cyclopropanecarboxaldehyde, the temperature of the alkylation reaction is 40-80° C.;

wherein when the alkylating reagent in step (3) is cyclopropanecarboxaldehyde, the time of the alkylation reaction is 1.5-2.5 h;

wherein when the alkylating reagent in step (3) is cyclopropanecarboxaldehyde, the solvent of the alkylation reaction is one or a combination of at least two selected from the group consisting of ethyl acetate, toluene and xylene.

16. The preparation method according to claim 1, wherein in step (4), molar ratio of 2-fluoro-3-(alkylamino)-N-(4-(perfluoropropane-2-yl)-2-(trifluoromethyl) phenyl) benzamide to the acyl chloride compound as shown by formula II is 1:1 to 1:1.5;

wherein the reaction in step (4) is performed in the presence of a catalyst, and the catalyst is 4-dimethylaminopyridine;

wherein the used amount of the catalyst is 0.1%-5% by mass of 2-fluoro-3-(alkylamino)-N-(4-(perfluoropropane-2-yl)-2-(trifluoromethyl) phenyl) benzamide;

wherein the solvent of the reaction in step (4) is any one or a combination of at least two selected from the group consisting of dichloromethane, 1,2-dichloroethane, chloroform, benzene, toluene, xylene, chlorobenzene, and dichlorobenzene;

wherein in step (4), mass ratio of 2-fluoro-3-(alkylamino)-N-(4-(perfluoropropane-2-yl)-2-(trifluoromethyl)phenyl)benzamide to the solvent is: 1:2 to 1:8;

wherein the temperature of the reaction in step (4) is 40-180° C.;

wherein the time of the reaction in step (4) is 1-6 h.

17. The preparation method according to claim 16, wherein in step (4), molar ratio of 2-fluoro-3-(alkylamino)-N-(4-(perfluoropropane-2-yl)-2-(trifluoromethyl) phenyl) benzamide to the acyl chloride compound as shown by formula II is 1:1.05 to 1:1.1;

wherein the solvent of the reaction in step (4) is 1,2-dichloroethane or toluene;

wherein in step (4), mass ratio of 2-fluoro-3-(alkylamino)-N-(4-(perfluoropropane-2-yl)-2-(trifluoromethyl)phenyl)benzamide to the solvent is 1:4 to 1:6;

wherein the temperature of the reaction in step (4) is 80-110° C.;

wherein the time of the reaction in step (4) is 3-5 h.

18. The preparation method according to claim 17, wherein after the reaction in step (4) is completed, post-treatment is performed, and the post-treatment includes the following steps:

an alkali solution is added to the reaction system, stirred at 80° C. for 10-40 min, and subjected to phase separation while it was hot, to obtain 2-fluoro-3-(alkylbenzamido)-N-(4-(perfluoropropane-2-yl)-2-(trifluoromethyl)phenyl)benzamide;

wherein the alkali solution is one or a combination of at least two selected from the group consisting of aqueous solution of hydroxide, carbonate or bicarbonate of an alkali metal or an alkaline earth metal.

19. The preparation method according to claim 1, wherein the bromination reaction in step (5) is performed in the presence of bromide and oxidant;

wherein the bromide is one or a combination of at least two selected from the group consisting of an alkali metal bromide, an alkaline earth metal bromide, hydrobromic acid, bromine, and ammonium bromide;

wherein in step (5), molar ratio of 2-fluoro-3-(alkylbenzamido)-N-(4-(perfluoropropane-2-yl)-2-(trifluoromethyl) phenyl) benzamide to bromide is 1:0.55 to 1:2.0;

wherein the oxidant is one or a combination of at least two selected from the group consisting of chlorine gas, perchlorate, chlorate, chlorite, or hypochlorite of alkali metal or alkaline earth metal;

wherein in step (5), molar ratio of 2-fluoro-3-(alkylbenzamido)-N-(4-(perfluoropropane-2-yl)-2-(trifluoromethyl) phenyl) benzamide to oxidant is 1:0.2 to 1:2.0;

wherein the bromination reaction in step (5) is performed in the presence of an alkaline substance;

wherein the alkaline substance is one or a combination of at least two selected from the group consisting of hydroxide, carbonate and bicarbonate of an alkali metal or an alkaline earth metal;

wherein molar ratio of 2-fluoro-3-(alkylbenzamido)-N-(4-(perfluoropropane-2-yl)-2-(trifluoromethyl) phenyl) benzamide to the alkaline substance is 1:0 to 1:3.0;

wherein the temperature of the bromination reaction in step (5) is 0-150° C.

20. The preparation method according to claim 19, wherein the bromide is sodium bromide or hydrobromic acid;

wherein in step (5), molar ratio of 2-fluoro-3-(alkylbenzamido)-N-(4-(perfluoropropane-2-yl)-2-(trifluoromethyl) phenyl) benzamide to bromide is 1:1.2 to 1:1.6;

wherein the oxidant is one or a combination of at least two selected from the group consisting of sodium chlorate, sodium hypochlorite and chlorine gas;

wherein in step (5), molar ratio of 2-fluoro-3-(alkylbenzamido)-N-(4-(perfluoropropane-2-yl)-2-(trifluoromethyl) phenyl) benzamide to oxidant is 1:0.4 to 1:1.6;

wherein the alkaline substance is sodium hydroxide or potassium hydroxide;

wherein molar ratio of 2-fluoro-3-(alkylbenzamido)-N-(4-(perfluoropropane-2-yl)-2-(trifluoromethyl) phenyl) benzamide to the alkaline substance is 1:0.5 to 1:2.8.

* * * * *